(12) United States Patent
Julstrom et al.

(10) Patent No.: US 11,894,819 B2
(45) Date of Patent: Feb. 6, 2024

(54) AUDIO MONITORING SYSTEM

(71) Applicant: Sensaphonics, Inc., Chicago, IL (US)

(72) Inventors: Stephen D. Julstrom, Chicago, IL (US); Michael J. Santucci, Oak Park, IL (US)

(73) Assignee: Sensaphonics, Inc., Chicago, IL (US)

( * ) Notice: Subject to any disclaimer, the term of this patent is extended or adjusted under 35 U.S.C. 154(b) by 0 days.

(21) Appl. No.: 17/176,016

(22) Filed: Feb. 15, 2021

(65) Prior Publication Data
US 2021/0257981 A1  Aug. 19, 2021

Related U.S. Application Data

(60) Provisional application No. 62/978,102, filed on Feb. 18, 2020.

(51) Int. Cl.
*H03G 3/30* (2006.01)
*H04R 1/10* (2006.01)
(Continued)

(52) U.S. Cl.
CPC ........... *H03G 3/3005* (2013.01); *A61F 11/08* (2013.01); *G06F 3/165* (2013.01); *H03G 5/165* (2013.01);
(Continued)

(58) Field of Classification Search
CPC ... H04L 67/12; H04L 67/1097; H04L 1/0002; H04L 1/0041; H04L 1/18; H04L 5/0064; H04L 67/306; H04L 65/1069; H04L 29/06027; H04L 51/24; H04L 67/025; H04L 12/1818; H04L 65/4084; H04L 65/4092; H04L 65/602; H04L 67/141; H04L 67/28; H04W 12/06; H04W 4/35; H04W 4/18; H04W 12/033; H04W 64/006; H04W 12/02; H04W 8/18; H04W 8/20; H04W 24/02; H04W 72/02; H04W 12/086; H04W 24/00; H04W 24/10; H04W 68/00; H04W 92/18; H04W 52/362; H04W 48/08; H04W 8/245; H04W 36/08; H04W 4/48;
(Continued)

(56) References Cited

U.S. PATENT DOCUMENTS 5,276,739 A * 1/1994 Krokstad ............. H04R 25/453
                                                            381/83
6,754,359 B1 * 6/2004 Svean .................. H04R 1/1083
                                                            381/313
(Continued)

*Primary Examiner* — Lun-See Lao
(74) *Attorney, Agent, or Firm* — Bishop, Diehl & Lee, Ltd

(57) ABSTRACT

An integrated system for hearing protection and enhancement having earpieces including microphones and receivers to provide for user control of ambience level (mic gain), monitor input, control over limiting of excessive levels, and frequency equalization, all with very wide input dynamic range capability and controlled output dynamic range. The user control comprises a wired or wireless smartphone app. Also, the wide input dynamic range is achieved by placement of limiter circuitry capable of handling the entire input dynamic range prior to the most dynamic range limited circuit blocks: digital EQ block, output amplifier, earpiece receiver, and the users' ears. Switches allow combining left and right signals to be directed to a user's favored ear, if necessary.

23 Claims, 11 Drawing Sheets

(51) Int. Cl.
  *G06F 3/16* (2006.01)
  *H04R 1/08* (2006.01)
  *A61F 11/08* (2006.01)
  *H03G 5/16* (2006.01)
  *H04R 3/00* (2006.01)

(52) U.S. Cl.
  CPC ............ *H04R 1/08* (2013.01); *H04R 1/1016* (2013.01); *H04R 1/1041* (2013.01); *H04R 1/1083* (2013.01); *H04R 3/007* (2013.01); *H03G 2201/103* (2013.01); *H04R 2420/07* (2013.01); *H04R 2430/01* (2013.01)

(58) Field of Classification Search
  CPC ............ H04W 48/16; H04W 52/0251; H04W 52/028; H04W 80/04; H04W 84/20; H04W 4/21; H04W 4/24; H04W 48/12; H04W 56/001; H04W 72/0446; H04W 74/0816; H04W 76/15; H04W 88/04; H04W 12/068; H04W 12/126; H04R 29/00; H04R 2420/09; H04R 5/027; H04R 1/1066; H04R 2410/05; H04R 1/028; H04R 25/453; H04R 1/10; H04R 2205/041; H04R 25/55; H04R 25/604; H04R 2201/401; H04R 5/0335; H04R 1/1058; H04R 2201/023; H04R 2420/05; H04R 1/086; H04R 2225/0216; H04R 2499/15; H04R 25/556; H04R 1/08; H04R 19/005; H04R 2203/12; H04R 25/75; H04R 3/02; H04R 25/356; H04R 3/14; H04R 2227/005; H04R 2420/01; H04R 25/405; H04R 1/24; H04R 25/652; H04R 29/005; H04R 9/06; H04R 2225/021; H04R 2430/03; H04R 2460/11; H04R 25/658; H04R 29/008; H04R 3/007; H04R 17/00; H04R 25/609; H04R 3/002; H04R 2225/0213; H04R 2225/49; H04R 2400/11; H04R 29/004; H04R 1/023; H04R 1/2807; H04R 1/2811; H04R 1/34; H04R 19/04; H04R 25/02; H04R 25/656; H04R 2201/025; H04R 2205/022
  USPC .............................................. 381/74, 92, 72
  See application file for complete search history.

(56) References Cited

U.S. PATENT DOCUMENTS

| | | | |
|---|---|---|---|
| 8,855,343 B2* | 10/2014 | Usher | H03G 9/18 |
| | | | 381/317 |
| 9,807,521 B2* | 10/2017 | Werner, Jr. | H04R 25/407 |
| 11,550,535 B2* | 1/2023 | Goldstein | G06F 3/16 |
| 2018/0151187 A1* | 5/2018 | Sørensen | H04L 41/0896 |
| 2020/0344545 A1* | 10/2020 | Hvidsten | G06F 3/165 |

* cited by examiner

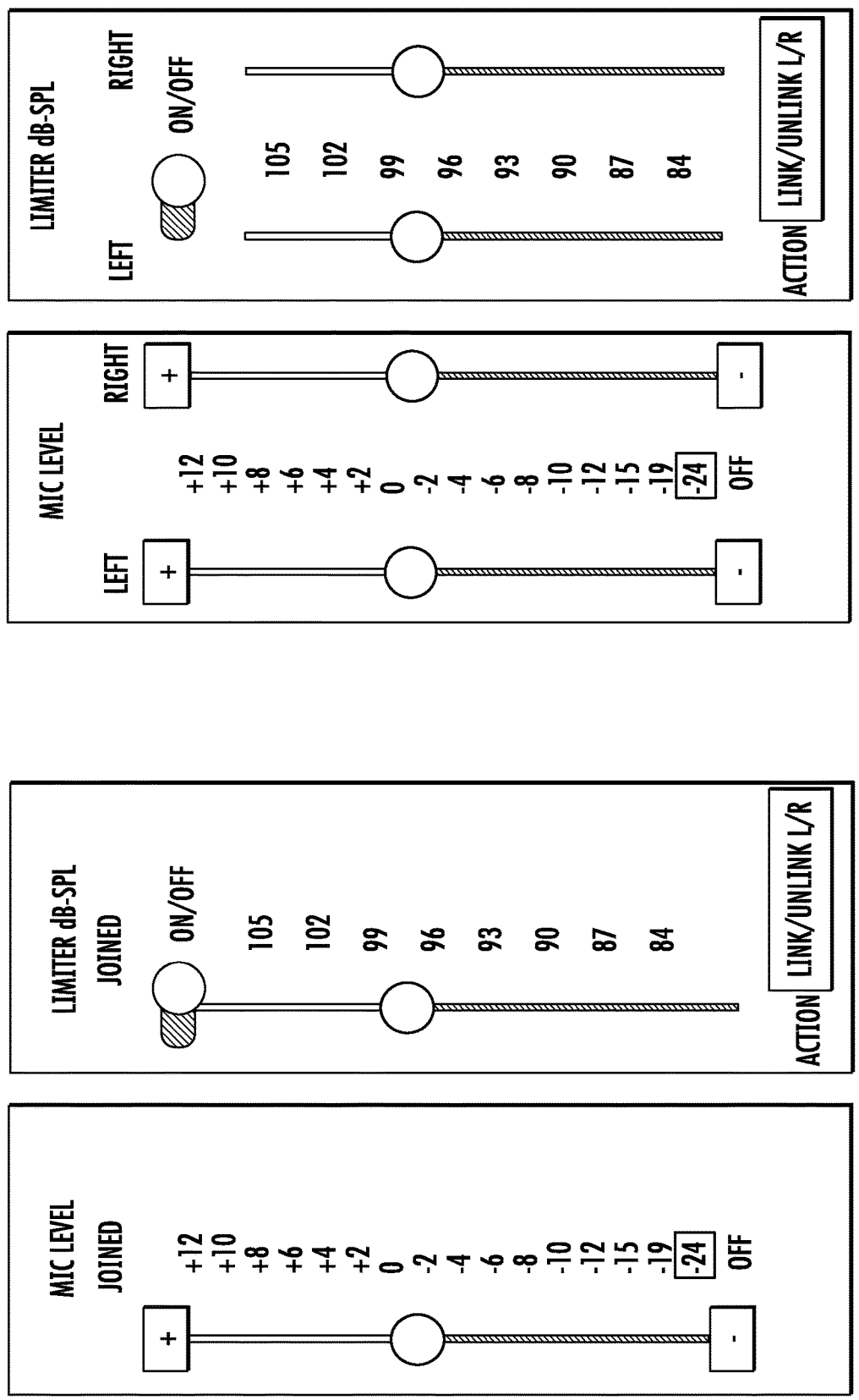

AUDIO MONITORING SYSTEM

RELATED APPLICATIONS

The present application claims the filing priority of U.S. Provisional Application No. 62/978,102, titled "AUDIO MONITORING SYSTEM" and filed on Feb. 18, 2020. The '102 application is hereby incorporated by reference.

TECHNICAL FIELD OF THE INVENTION

The present invention relates to earphone monitoring systems, and in particular, to a system that provides extensive user control of both ambient and monitored sound characteristics enabling both hearing protection and hearing enhancement. U.S. Pat. No. 8,160,261 is hereby incorporated in its entirety.

BACKGROUND OF THE INVENTION

Performing musicians need to be able to hear their own instrument or voice, and the instruments and voices of other musicians performing with them. There may also be a need for hearing protection against excessive sound levels and enhancement of the reproduced sound, both for preference and for hearing compensation.

For electronically amplified music, it has become common practice for performers to receive their desired audio through earpieces that seal the ear canal from outside sound. This external ambient sound may be very loud on the performance stage, especially if monitoring sound from loudspeakers is purposely directed at the performers, as was common practice until more recent years. With earpiece monitoring, the performer's desired sound mix is typically received through a wireless body-worn receiver from a mix created off-stage from the various audio inputs. The sound level for the performer can then preferably be set to a lower, safer level than would be experienced without sealed ears.

Sealed ears, though, near-totally isolate the performer from the ambient stage and audience sound, which is generally not desired, either. U.S. Pat. No. 8,160,261 to Schulein et al. (the '261 Patent), assigned to the Assignee of the present application, addressed this problem by including wide dynamic range microphones in the earpieces, with electronic control over the typically attenuated microphone signal returned to the ear canal. The invention also included limiters to protect against very high-level sounds from both the monitor input and the microphone (ambience) input.

Performers of non-amplified music can also experience excessive sound levels, especially in large ensembles such as symphony orchestras, and could benefit from hearing protection that does not interfere with their playing and sense of ensemble. Additionally, musicians of all kinds can experience hearing issues and deficiencies, often to the extent that performing becomes difficult or impossible. "A Solution to Challenges Faced by Hearing-impaired Musicians Performing on Loud Amplified Stages", Larry Revit, Hearing Review, Jul. 30, 2014 reviews the difficulties that hearing-impaired musicians can experience and describes a system of outboard equipment providing gain, frequency equalization, additional limiting, and source mixing that could be used in conjunction with the prior referenced invention.

It is the purpose of the present invention to provide solutions to the challenges addressed by the prior referenced invention, but also to provide integrated capabilities for hearing enhancement for both preference and hearing correction, along with greater flexibility in hearing protection parameters. These goals need to be accomplished while maintaining very wide dynamic range capability over the various user parameter settings, accurate sound reproduction with low latency under all conditions, compactness and portability, and straightforward, but flexible user interface.

SUMMARY OF THE INVENTION

There is disclosed herein an improved furniture assembly which avoids the disadvantages of prior devices while affording additional structural and operating advantages.

Generally speaking, an integrated system for hearing protection and enhancement comprises earpieces having microphones and receivers to provide for user control of ambience level (mic gain), monitor input, control over limiting of excessive levels, and frequency equalization, all with very wide input dynamic range capability and controlled output dynamic range.

In specific embodiments, the user control comprises a wired or wireless smartphone app. Also, the wide input dynamic range is achieved by placement of limiter circuitry capable of handling the entire input dynamic range prior to the most dynamic range limited circuit blocks: digital EQ block, output amplifier, earpiece receiver, and the users' ears.

In specific embodiments of the integrated system, the limiter is placed after the mic gain resistors to prevent overload with mic gain increases. Further, the integrated system may comprise a limiter that responds to the short-term average signal level appearing at the user's ears, with selectable threshold settings.

In other specific embodiments, the integrated system senses the short-term average signal level after the EQ block and all gain-altering signal stages, but limits earlier, as above. Also, the system is sensitive to the approximate A-weighted short-term average signal level.

In still other specific embodiments, the integrated system further comprises at least one of the following features, including separate or joined left right control of mic gain, limiter threshold, EQ; linked or unlinked left/right limiter action; body pack mic gain switches for either stepwise or toggle mode control; and CROS connection capability.

These and other aspects of the invention may be understood more readily from the following description and the appended drawings.

BRIEF DESCRIPTION OF THE DRAWINGS

For the purpose of facilitating an understanding of the subject matter sought to be protected, there are illustrated in the accompanying drawings, embodiments thereof, from an inspection of which, when considered in connection with the following description, the subject matter sought to be protected, its construction and operation, and many of its advantages should be readily understood and appreciated.

FIGS. 9*a* and 9*b* are examples of smartphone app screens for control of microphone gain and limiter.

DETAILED DESCRIPTION OF AT LEAST ONE PREFERRED EMBODIMENT

The following descriptions of detailed embodiments are for exemplifying the principles and advantages of the inventions claimed herein. They are not to be taken in any way as limitations on the scope of the invention.

Figure 1:
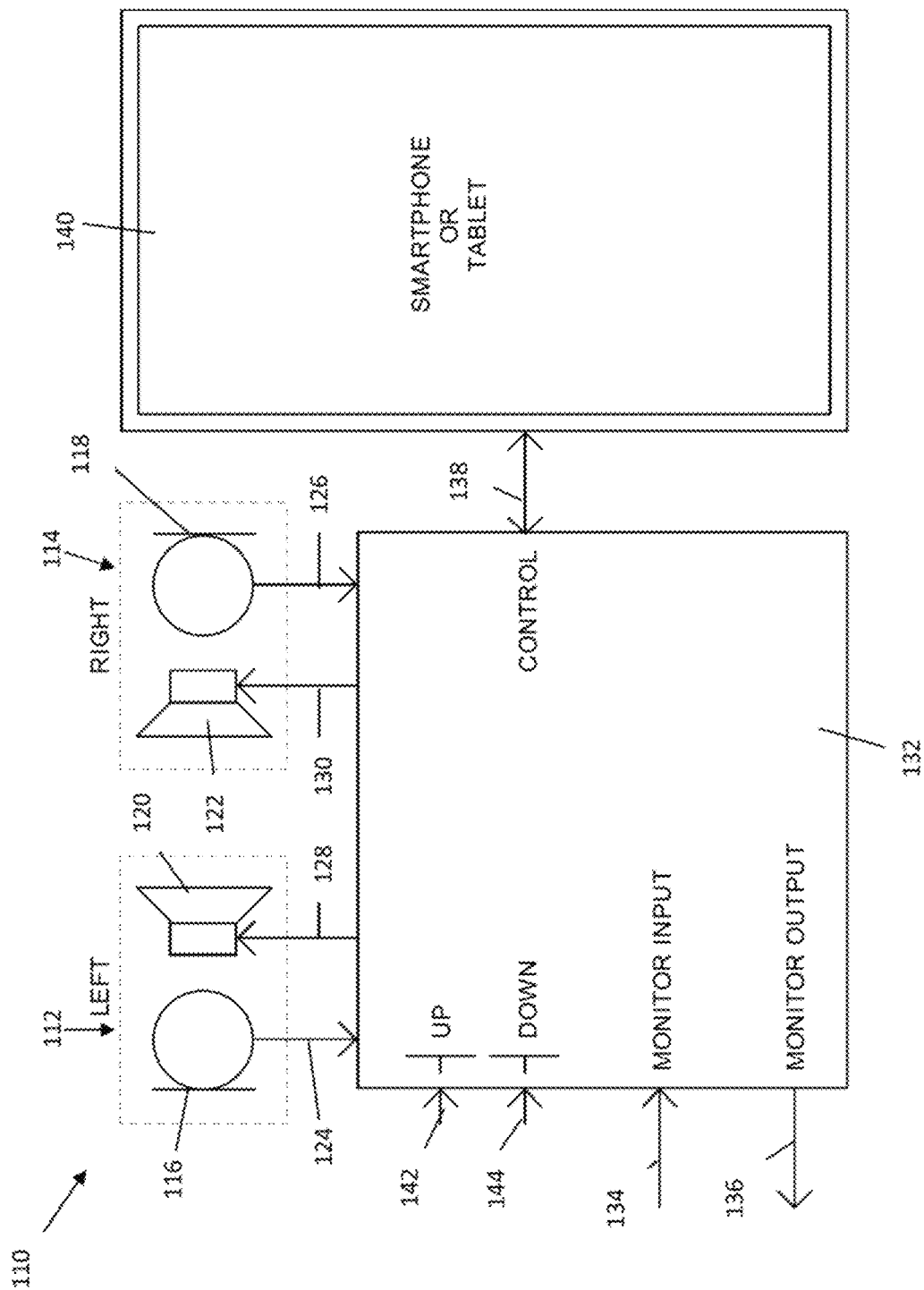
FIG. 1 is a diagram showing the basic components of a system in accordance with the present invention and a simplified indication of their interconnection.

Turning to FIG. 1, the basic constituent parts of an audio monitoring system 110 in accordance with an embodiment of the present invention are shown from an external perspective. Similar to the prior referenced invention, left 112 and right 114 earpieces, each containing an outward-facing microphone with associated buffer circuitry 116, 118 and an inward-facing receiver with associated series impedance 120, 122, connect by preferably bundled wires 124, 126, 128, 130 to the body pack 132, which is the central signal processing unit. The body pack also accepts left and right monitor input signals 134 and also produces left and right monitor output signals 136. There is a control interface 138 to a smartphone or tablet 140, which may be wired, typically through a USB connection, or wireless, typically through a Bluetooth connection. The associated smartphone application allows the user to set the various operating parameters, which are then remembered in the body pack so that the smartphone may be disconnected in use. The body pack's embedded firmware uses these stored settings to control the behavior of the various analog and digital functions of the body pack. In use, the available basic user controls are the microphone gain up 142 and down 144 buttons. These are located at the top of the body pack in a manner that allows their operation by feel.

A significant challenge to the design of such a system is the achievement of a very wide dynamic range throughout the signal path, maintaining a low noise floor and appropriately high overload point over the range of parameter settings available to the user. A novel method of achieving this goal will become apparent in the following descriptions.

Figure 2:
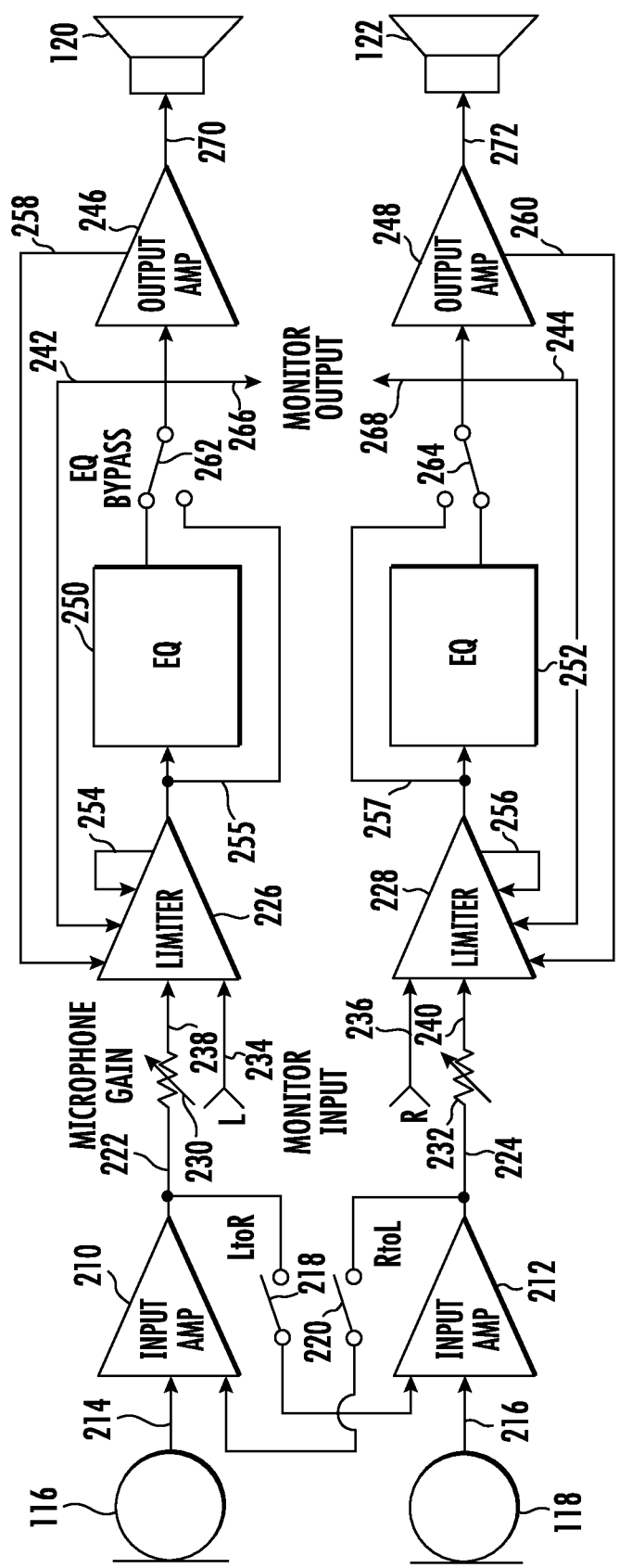
FIG. 2 is a simplified block diagram illustrating the signal flow of such system.

FIG. 2 shows the basic signal flow of the embodiment. Left 210 and right 212 input amplifiers accept the buffered left 214 and right 216 earpiece microphone signals. Software-controlled switches 218, 220 provide for the option of feeding the left microphone signal to the right channel to combine with the right microphone signal or feeding the right microphone signal to the left channel to combine with the left microphone signal. These signal-routing possibilities are referred to as CROS (Contra-Lateral Routing of Signal) connections. This option is intended for users with useful hearing in one ear only, enabling them to hear sounds from both sides equally well by routing both microphone signals to the better ear.

The left 222 and right 224 channel input amplifier output signals continue on to the left 226 and right 228 limiter stages through the left 230 and right 232 microphone gain controls. These allow for software control of the insertion gain (electroacoustic system gain compared to open ear) in mostly 2 dB steps from +12 dB down to −24 dB and off. The left and right microphone gain settings can be set together to the same gain (joined) or set independently (separated). In typical use, those who wish to match an open-ear sound level and whose major need is only the limiter function would likely leave the microphone gain settings at 0 dB. Those with some hearing loss may prefer higher settings. The negative settings may be used in the presence of louder unamplified instruments, but are especially useful for sound-stages with loud, electronically amplified instruments. Negative settings reduce the ambient sound level for hearing protection, but also so that the desired monitor mix can dominate over the ambient stage sound.

As mentioned in connection with FIG. 1, the body pack up/down switches 142, 144 allow the performer to step the microphone gains up and down without needing the smartphone app to be connected. Another software option is to have the up and down buttons each represent specific user-selected microphone gain settings that the switches toggle between. An example of this usage would have the down button represent a specific low, negative microphone gain setting for use while performing, and the up button represent a higher gain, perhaps 0 dB, to enable better communication amongst musicians, etc. between musical pieces.

The left 234 and right 236 monitor input signals are inserted into the left and right limiters, along with the gain-adjusted left 238 and right 240 microphone signals. No separate gain controls are provided for the monitor inputs, as the signal levels are controlled by the source of these signals.

Figure 3:
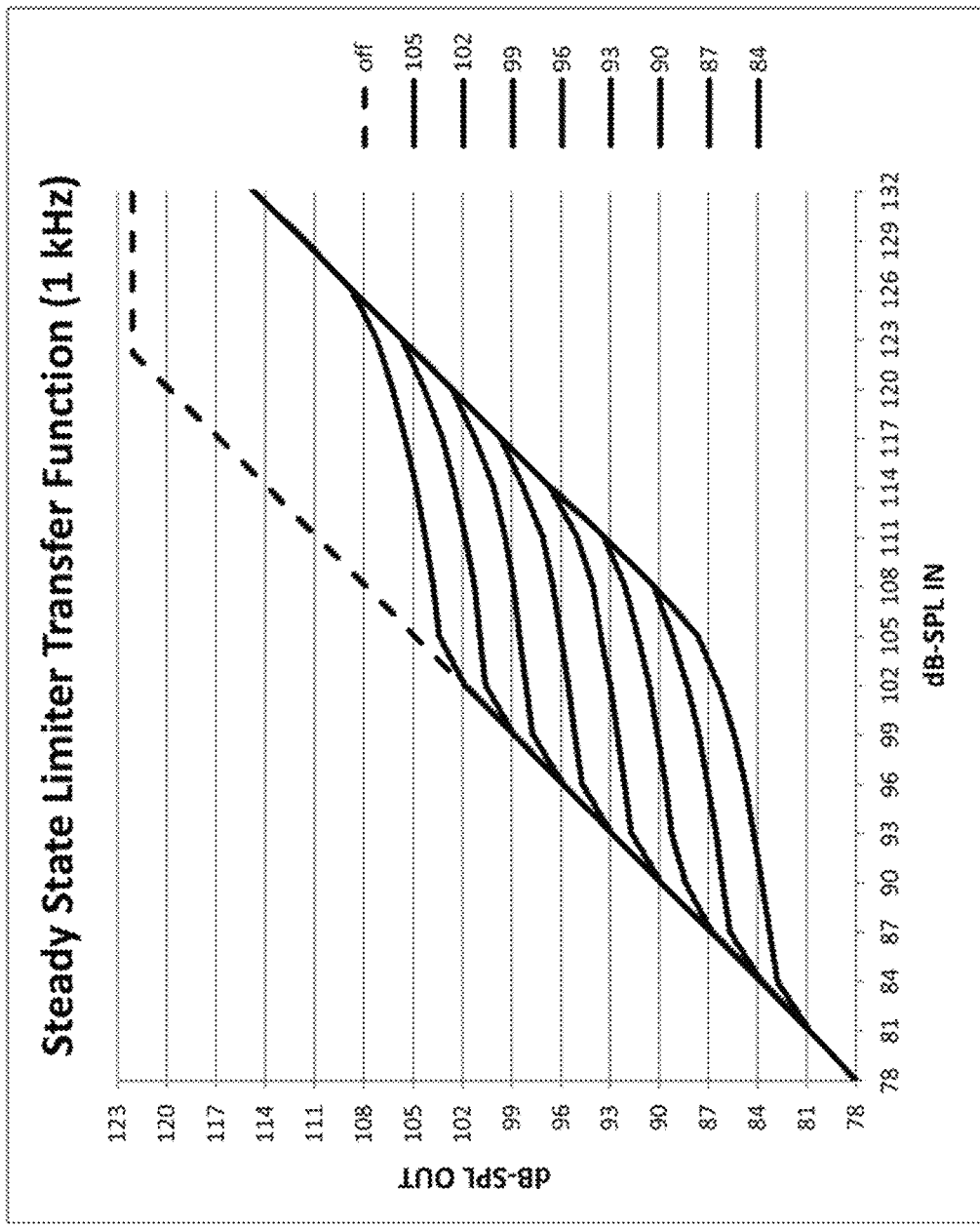
FIG. 3 is graph showing the stead-state 1 kHz transfer function of a limiter in such system at various threshold settings.

The left and right limiters serve dual functions. The primary function is to reduce the level of signals that would produce uncomfortably loud or harmful sound levels in the user's ears. The loudness threshold for limiting can be set by the user through the smartphone app, in relation to their needs and preferences. FIG. 3 plots the 1 kHz steady-state output level vs. input level at the 0 dB microphone level setting for the various threshold settings. The frequency response of the level measurement portion of the limiting circuitry roughly follows the A-weighting curve (specified in IEC 61672:2003). The level measurement is of a short-term average, with an adaptive attack time that becomes faster with higher level, more percussive sounds.

Returning to FIG. 2, the left 242 and right 244 level-measurement signals are also the inputs to the left 246 and right 248 output amplifiers, where the relationship between the signal level and the reproduced earpiece level is fixed, irrespective of any changes induced by any level or gain changes before these points. Thus, the short-term average, approximately A-weighted sound level reaching the user's ears is limited to about the dB-SPL level set by the user. If the incoming sound level, as modified by the microphone gain settings, exceeds the threshold setting by more than 18 dB, the characteristic of the limiter is such that the maximum gain reduction is limited to 18 dB.

A secondary function of the limiter is to limit the dynamic range of the signal from the microphone or monitor input to what can be accepted by the following left 250 and right 252 frequency equalization (EQ) block, left and right output amplifiers, and left and right earpiece receivers without signal clipping or overload. As shown in FIG. 2, the signal is sensed in each channel at the left 254 and right 256 left and right limiter amplifier outputs, which are just above the level of the inputs to the left 255 and right 257 EQ circuit blocks, the left and right inputs to the left and right output amplifiers and left 258 and right 260 internal points in the left and right output amplifiers that could be subject to clipping under certain conditions of very high signal level. In contrast to the sensing for the first limiter function described above, this sensing is rapid and peak-sensing, intended to only activate when peak signal levels approach clipping. The 1 kHz steady state result is indicated by the limiter "off" curve (i.e., broken line curve) of FIG. 3. When signal levels corresponding to a 1 kHz 122 dB-SPL output level are reached, the gain is reduced to prevent an increase in level that would result in clipping or overload.

The left and right limiter thresholds can be set together to the same level (joined) or set independently (separated). When either or both of the left and right channel limiters are called on to limit a channel's signal level by reducing its gain, this limiter action may be linked between the channels so that the gain reduction occurs identically in the two channels, maintaining left-right binaural balance, or unlinked, so that the left and right limiters act totally independently.

Returning to FIG. 2, the left and right limiter outputs feed the left and right EQ blocks 250, 252. The EQ blocks consist of software-controlled seven-band graphic equalizers and are implemented in a known manner with digital signal processing (DSP), in differentiation from the rest of the circuitry, which is implemented with analog circuitry. The dynamic range considerations associated with this block will be discussed in reference to FIG. 4. Staying with FIG. 2, software-controlled switches 262, 264 allow for complete bypass of the left and right digital EQ blocks, for use when the EQ is not needed or desired.

The left 266 and right 268 monitor outputs are taken after these switches, from the inputs to the output amplifiers. As discussed above, the signals at these points represent the sound reaching the user's ears. One use for these outputs is to monitor the indicated sound levels for hearing safety evaluation.

Finally, the left and right output amplifiers 246, 248 provide appropriate left 270 and right 272 drive signals to the earpiece receivers 120, 122. The output amplifiers provide extensive fixed frequency response equalization to combine with and modify the receiver's inherent response to yield the desired net input-to-output frequency response that mimics the open ear's response. The previously referenced '261 Patent provides additional discussion of this topic and is hereby incorporated by reference.

In addition to maintaining an accurate frequency response, a challenge is to maintain a wide dynamic range from input to output, sufficient for the wide variety of sound sources expected, and to maintain this over the range of control possibilities provided. First, the earpiece microphone and its associated circuitry must maintain a low self-noise floor while achieving a very high acoustic overload point. The '261 Patent discloses a modified Knowles EK-3133 electret microphone with a specified typical self-noise of 24 dBA-SPL. The microphone of that disclosed device was modified and used in a novel high-voltage circuit to achieve an acoustic overload point of greater than 140 dB-SPL. Levels approaching this at the musician's ears can come from amplified instruments and non-amplified percussive instruments.

Conversely, an embodiment of the present invention utilizes a newer MEMS (microelectromechanical systems) microphone, the TAOT model 19014A. This microphone also has a typical self-noise specification of 24 dBA-SPL and an overload of 135 dB-SPL, 111 dB above its noise floor. While the overload point is slightly lower than the microphone as disclosed in the '261 Patent, it is still adequate for all but the most extreme circumstances, without requiring a high-voltage supply and showing improved environmental robustness.

As will be detailed in connection with FIG. 6, the microphone signal is buffered in the earpiece and sent to the body pack differentially over two wires, which also provide power from the body pack. The low-impedance buffered differential signal avoids hum and noise pickup and coupling from the receiver drive differential signal in the same cable. Thus, the cable connecting the earpieces to the body pack can remain unshielded, for the best user feel and comfort.

The quality and dynamic range of the microphone signal received by the body pack needs to be maintained throughout the system, with the exception that the receiver output signal does not need to and should not reach 135 dB-SPL. The method of achieving the dynamic range goals is discussed in relation to FIG. 4, which shows the left channel signal flow in greater detail. It is important to keep in mind that each stage along the way adds its own noise. To avoid degrading the noise floor by more than 1 dB, the noise of a following stage must be at least 6 dB below the incoming noise. All noise measurements in the following discussion are assumed to be A-weighted.

Figure 4:
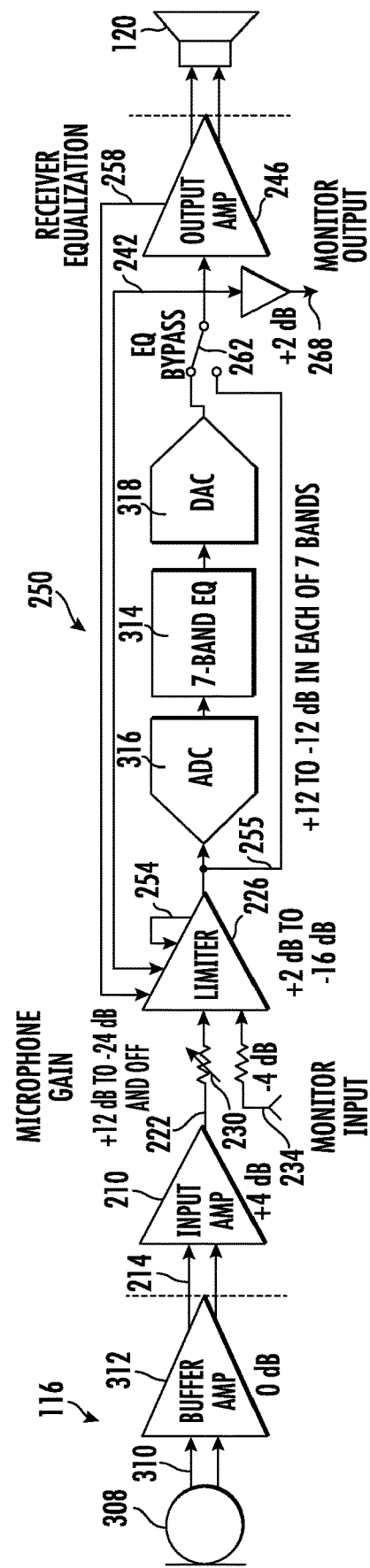
FIG. 4 is a more detailed block diagram illustrating the signal flow and gain structure of the left channel of such system.

Referring to FIG. 4, left earpiece microphone 308 outputs differential signals 310 to buffer amplifier 312, located in the left earpiece. This 0 dB gain buffer amplifier adds negligible noise to the microphone self-noise, so that noise comes into the body pack differentially with buffered differential signal 214 to left input amplifier 210 with a differential noise voltage level of −108 dBV, 70 dB below the microphone's rated 94 dB-SPL sensitivity of −38 dBV. The body pack left input amplifier accepts the earpiece's buffered differential microphone signal and amplifies it by 4 dB, which raises the maximum microphone signal level of +3 dBV to +7 dBV (3.17 Vpeak), still within the stage's output capability when operating on typically at least +1-3.3 Volt supplies. The input amplifier would add 1 dB to the microphone noise floor, but it also includes a modest high-frequency roll-off to compensate for a rise in the microphone frequency response at high frequencies, which brings the noise back down 1 dB. The noise floor at the output of the input amplifier is −104 dBV, 4 dB above the incoming noise floor, but still representing 24 dBA-SPL, and the full microphone dynamic range of 111 dB is maintained.

The input amplifier output signal 222 then goes to the left limiter 226 through left microphone gain control 230, consisting of stepped resistors that determine the microphone gain. At a microphone gain setting of 0 dB, the net gain without limiting action to the limiter output 255 is +2 dB. The limiter adds 0.5 dB of noise at this setting, yielding −101.5 dBV of noise at its output, representing 24.5 dBA-SPL. At higher microphone gain settings, the noise level coming into the limiter will rise and show even less contribution from the minor noise of the limiter, still representing 24 dBA-SPL noise level referred to the input but appearing as a higher noise level at the system output. These higher microphone gain settings are most likely to be used as hearing correction by users with some degree of hearing loss and will not be experienced as excessive noise levels. Lower microphone gain settings are most likely to be used where there are excessive ambient levels. As the microphone gain setting is lowered, the output noise floor will sink down to the residual noise levels of the following stages, as will be discussed.

Especially with the higher microphone gain settings, but even with a 0 dB microphone gain setting, the loudest microphone levels could overload the limiter stage, partly because its output has been designed to match the input overload of the following EQ block 250, occurring at −1 dBV, which would also be subject to overload. However, the limiter amplifier output 254 is one of the places sensed for the approach of overload to rapidly bring in the gain limiting to prevent such an occurrence, as discussed above. Additionally, if the limiter has been engaged to one of its threshold settings, the level will most often have already been limited before the overload prevention limiting needs to come into play.

The EQ block is implemented digitally as a seven-band graphic equalizer through the capabilities of a Texas Instruments TLV320AIC3268 mini-DSP integrated circuit 314. Analog-to-digital converter (ADC) 316 and digital-to-analog converter (DAC) 318 on either side of the mini-DSP are advantageously combined in an AKM AK4558 CODEC integrated circuit, a representative low-power, high-quality converter. The combination of these two integrated circuits provides a low-power, low-latency, wide-dynamic range implementation of the EQ function. The dynamic range of the CODEC, specified as 108 dB typical, 100 dB minimum, while wide, would not be wide enough to avoid compromising the dynamic range of the system without embedding it in the signal flow as described herein.

When considering the combined effect of the ADC and DAC, the dynamic range of the EQ block (with the EQ settings at 0 dB) reduces by 3 dB to 105 dB typical, 97 dB minimum. It is necessary to place this block's noise floor well below its incoming signal's noise floor to avoid excessive degradation of this critical parameter. As discussed above, with the microphone gain setting at 0 dB, the incoming noise floor is −101.5 dBV. The EQ block's noise floor is 105 dB (typical) below its maximum level of −1 dBV, or −106 dBV typical, −98 dBV maximum. Added to the incoming noise, the noise at the output of the EQ block becomes −100.5 dBV typical, −95.5 dBV maximum, corresponding to 25.5 dBA-SPL typical, 29.5 dBA-SPL maximum. In practice, the maximum noise level would be very unlikely to be reached, requiring both the converter's ADC and DAC to be at their minimum dynamic range specification.

The final receiver EQ/output amplifier 246 adds less than 0.5 dB to the typical noise level just discussed, and even less to the EQ block-determined maximum noise level. The EQ block can be electrically bypassed as a control option, which removes the EQ block's noise contribution, dropping the typical final noise level 1 dB and eliminating the possibility of the EQ block's maximum noise contribution. This also establishes a fully analog signal path, which has the benefit of essentially no latency through the system. However, even with the EQ block engaged, the characteristics of the converter and the minimal digital signal processing required enable a low net latency of 350 uSec, equivalent to about 12 cm of acoustic transit distance in air.

As discussed, higher microphone gain settings above 0 dB result in inherent microphone noise becoming dominant over that of the other stages, yielding an equivalent input noise essentially that of the microphone alone, 24 dBA-SPL, although with output noise levels equal to this raised by the microphone gain setting. Lower microphone gain settings below 0 dB correspondingly allow the later stages' noise to become the dominant factor at the output. With very low microphone gain settings, the residual output noise reduces to 22 dBA-SPL typical with the EQ engaged and 18 dBA-SPL with the EQ bypassed. If the monitor input is used in conjunction with very low microphone gain settings, these output-referred noise levels raise only very slightly, due to a very slight increase in the noise level of the limiter stage when the monitor input is terminated.

As discussed, sensing at the limiter amplifier outputs feeds back to the limiter circuitry to guard against clipping at this circuit point. Following this, the signal could undergo level increases through the EQ block due to user adjustment, which could result in clipping at the EQ block DAC without further precaution. The onset of potential clipping is effectively sensed at this point (when the EQ is switched in by EQ bypass switch 262) by sensing at the output amplifier input 242 for feedback to the limiter, which can then reduce the signal level at the EQ block input sufficiently to prevent clipping at the EQ block output.

The EQ block is followed by the output amplifier 246, which includes fixed frequency response equalization to force the receiver to deliver the appropriate wideband frequency response to the user's ear canal. The signal 242 at the input to the output amplifier has a fixed relationship to the acoustic output signal and reflects the level and the subjective frequency response that the user will experience. The sensed signal at this point feeds back to the limiter not just for the purpose of clipping protection, but also, importantly, to provide the reference signal for the primary limiter function according to the user threshold settings, as described with reference to FIG. 3.

The third sensed signal 258 for the limiter comes from an intermediate point in the output amplifier and prevents premature clipping at very high levels that might not be prevented by the sensing at the other two circuit points, depending on EQ block settings and the spectral content of the audio signal through the output amplifier.

As described, the circuit topology and associated level scaling enables maintenance of the full 135 dB-SPL input overload capability over a wide range of user settings, while not degrading the microphone's low self-noise and maintaining a wide, accurate frequency response to deliver natural, realistic sound for both the ambient sound field through the earpiece microphones and a monitor mix through the monitor input, all at very low or essentially zero latency. All this is accomplished while providing for user control over microphone gain, system frequency response, and level limiting, for both hearing safety and enhancement.

FIGS. 5-8 illustrate in more detail specific embodiments of circuitry which accomplishes the functionality of the previous figures.

Figure 5:
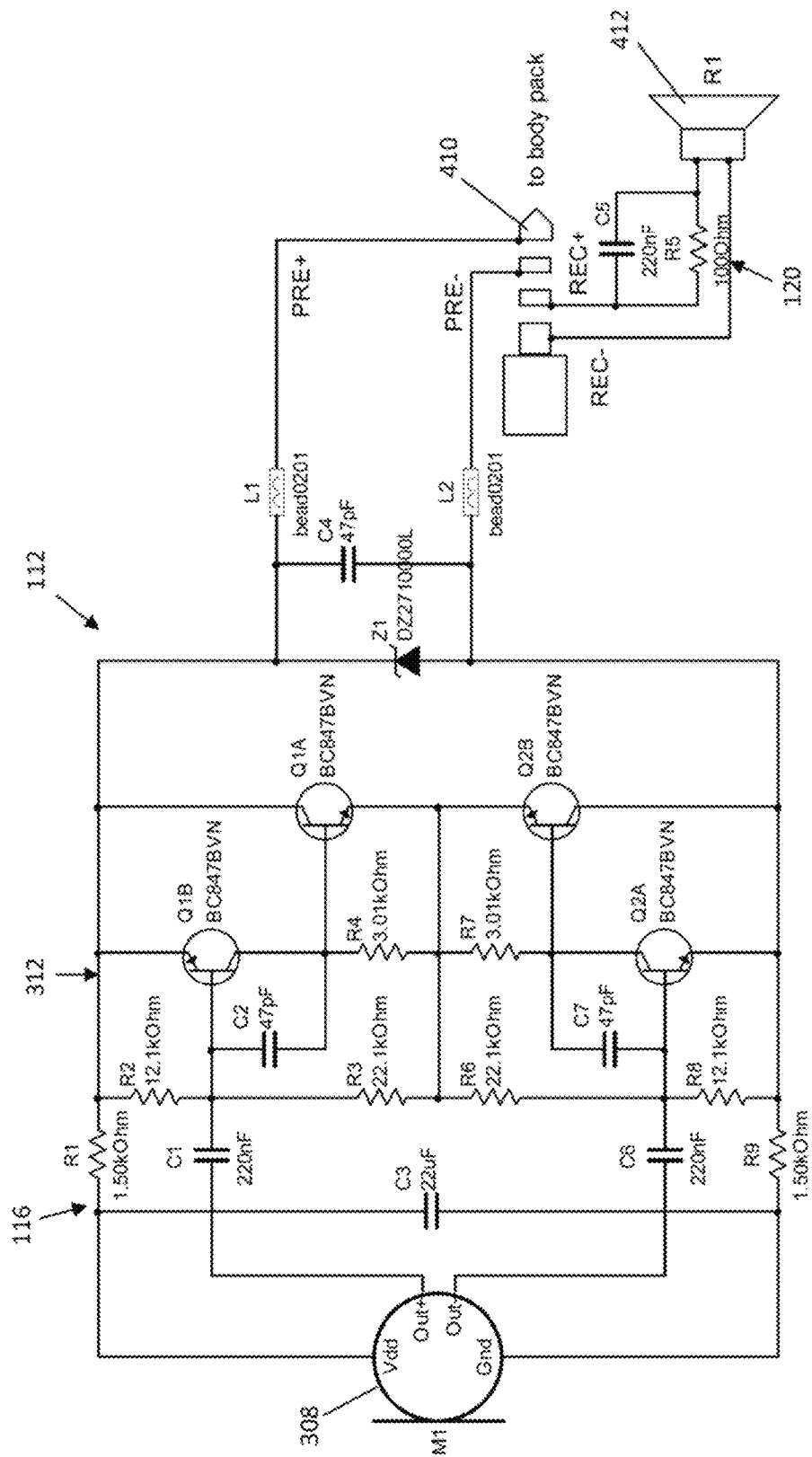
FIG. 5 is a schematic diagram of an earpiece of such system.

FIG. 5 shows the circuitry contained within the left earpiece 112, along with connections to the plug 410 to the body pack at the end of the earpiece-to-body pack cabling. The positive signal of the differential output of microphone 308 is buffered by a portion of unity gain buffer amplifier 312 made up of Q1A, Q1B and associated components. Likewise, the negative signal output of the microphone is buffered by the other portion of the unity gain buffer amplifier made up of Q2A, Q2B and associated components. Together, the microphone and buffer stages deliver a differential signal down two wires of the connecting cable while providing a very low 2.5 Ohm differential output impedance. This very low impedance differential signal, combined with the balanced differential input amplifier 210 (FIG. 4), enables the microphone signal to be sent to the body pack without interference from hum and noise pickup or coupling from the receiver drive signals bundled in the same cable. A 2 mA supply current for the buffer circuitry and microphone is fed differentially from the body pack on the same two wires that carry the buffered differential microphone signal. The remaining two wires from the body pack to the left earpiece feed the differential output signal from output amplifier 246 (FIG. 4) through C5 and R5 to the left receiver 412. C5 and R5 make the impedance characteristics of their combination with the receiver more uniform with frequency and reduce the amount of response equalization in the output amplifier needed to achieve the desired electroacoustic frequency response.

Figure 6:
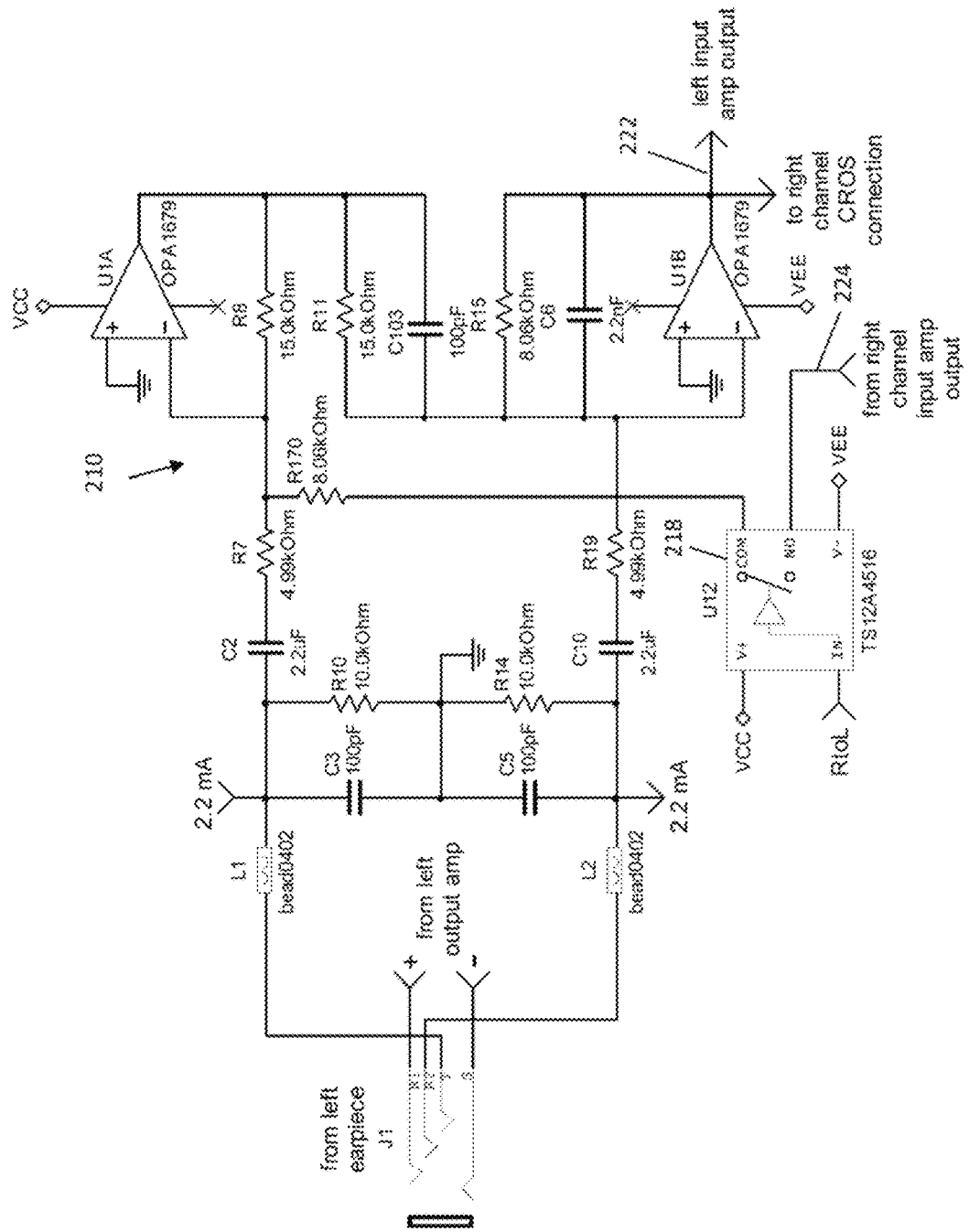
FIG. 6 is a schematic diagram of the input stage of such system.

FIG. 6 shows the circuitry of left input amplifier 210 (FIG. 4). 2.2 mA is sourced to and sunk from the connections to the earpiece microphone buffer amplifier. 0.2 mA of this current is used locally through R10, R14 to maintain the DC operating point symmetrically around ground, with the remainder of the current powering the earpiece microphone and buffer amplifier. U1A, U1B and associated components make up the input amplifier proper, providing a balanced, differential input, 4 dB of gain, and, with C6, a high frequency roll-off to compensate for a rise in the high frequency response of the microphone. Switch U12 218, under software control, provides, with R170, the CROS connection path from the right channel input amplifier output 224 to a left channel input amplifier input. This right channel signal can then appear at the left channel input amplifier output 222 at the same level that it appears at the right channel input amplifier output.

Figure 7:
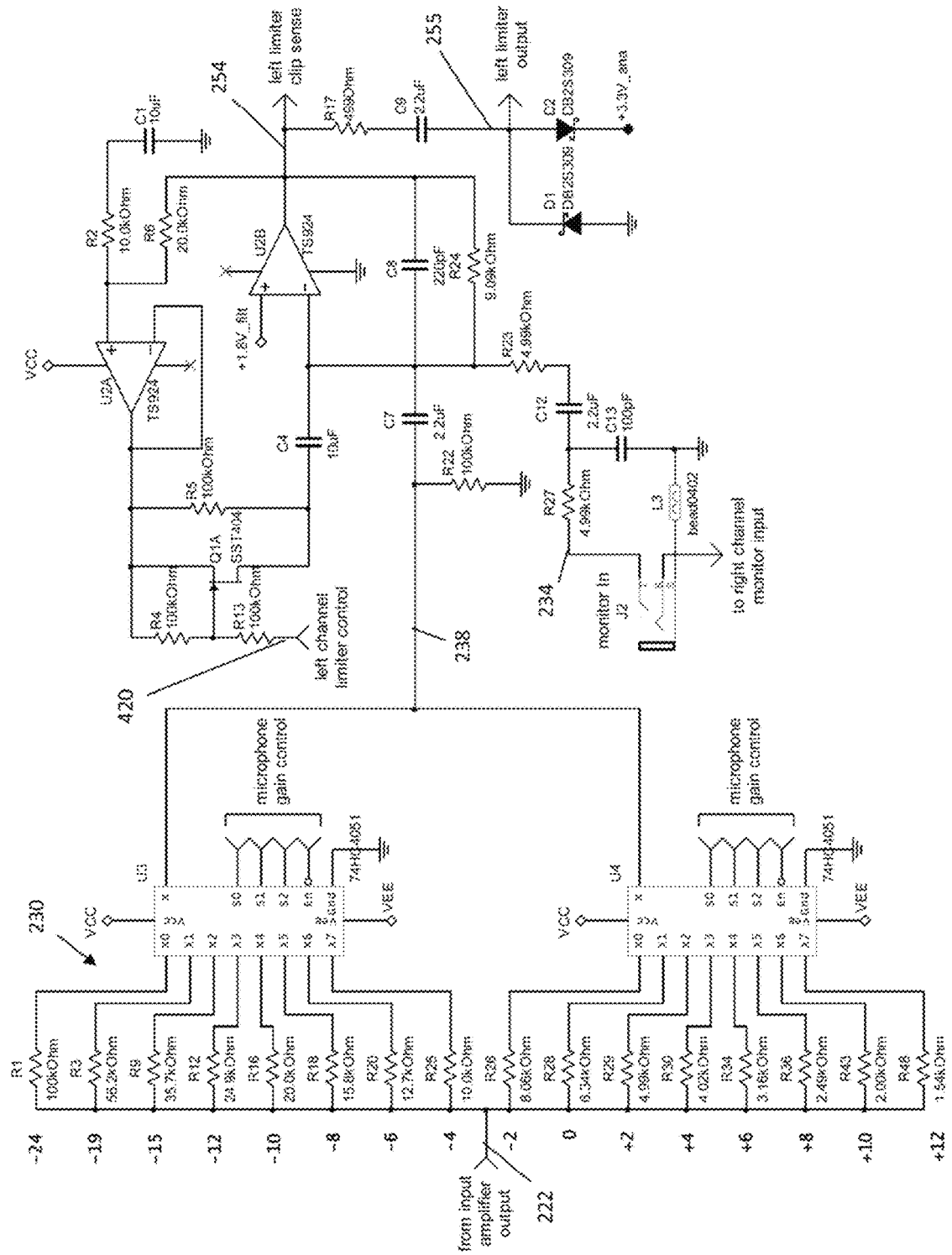
FIG. 7 is a schematic diagram of the left channel limiter amplifier circuitry of such system.

FIG. 7 shows left microphone gain control 230, left monitor input 234, and the signal amplifier portion of left limiter 226. The signal is received from the left input amplifier and fed to the left limiter amplifier U2A, U2B and associated components through a series resistor selected under software control by analog switches U3, U4, thus determining the net gain of the limiter, in the absence of any gain reduction due to limiting action. The left monitor signal is input into the left limiter amplifier at fixed gain. U2A, U2B operate at reduced supply voltages of VCC and ground. In combination with diodes D1, D2, this helps to prevent overdrive of the ADC input following left limiter output 255. Left limiter amplifier output 254 is the first of three clip sense points that feeds the left limiter drive circuitry of FIG. 8.

Staying with FIG. 7, Q1A is one of a pair of matched N-channel junction field-effect transistors, preferably the Linear Systems or Calogic SST404, (the other transistor is part of the right channel limiter) that acts as a voltage-controlled resistor. As the voltage at left channel limiter control 420 becomes more positive, the resistance of Q1A between its drain and source lowers, providing more negative signal feedback and reducing the net gain of the limiter amplifier. Voltage divider R2, R6 scales down the signal level that the JFET sees to reduce nonlinear signal distortion. Divider R4, R13 acts to balance out possible second harmonic nonlinear distortion generated by the JFET, in a known manner. The net effect of the JFET's action is to control the net gain of the limiter amplifier, from a microphone signal gain at the 0 dB microphone gain setting of +2 dB without limiting to a minimum of −16 dB at full limiting.

Figure 8:
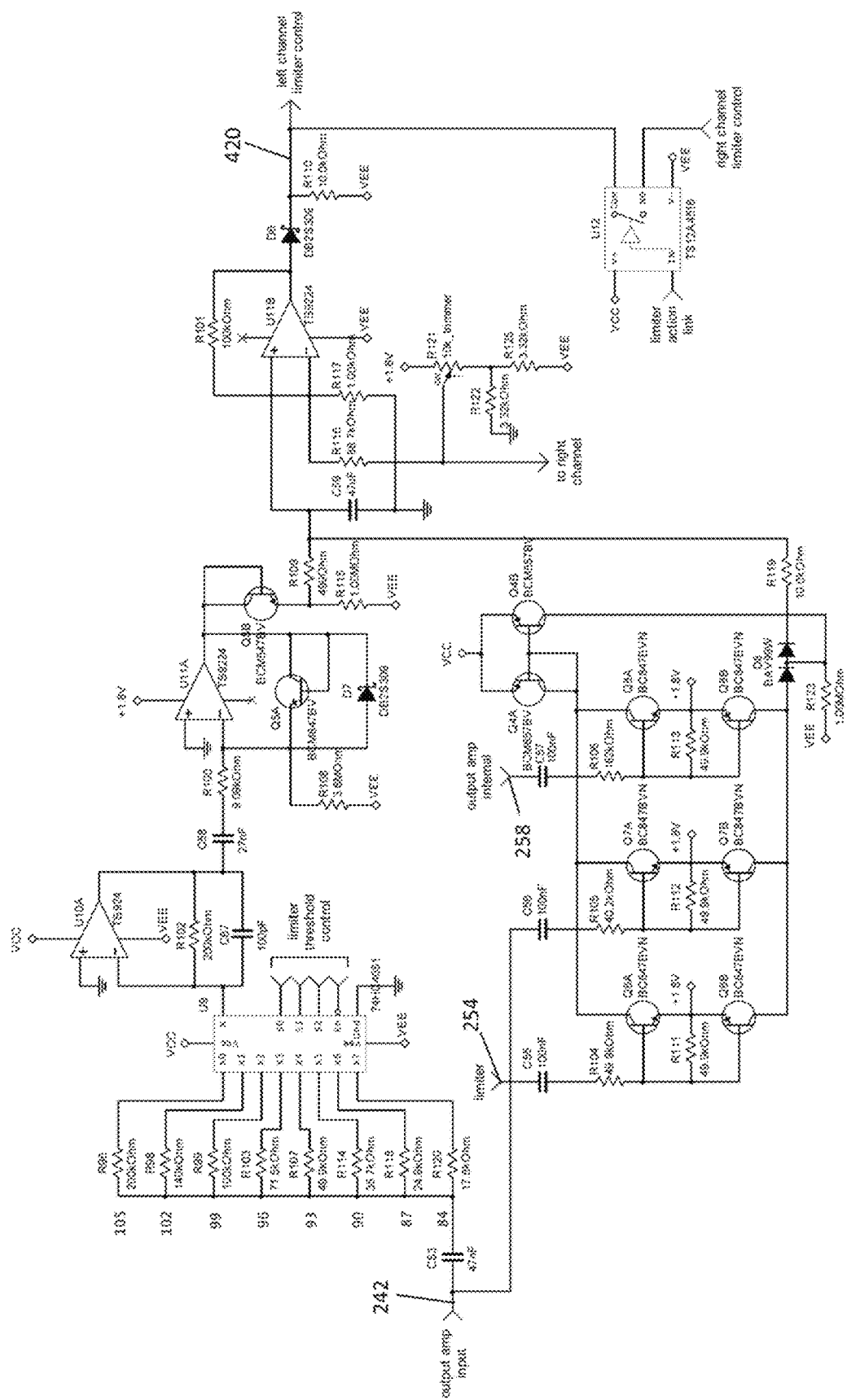
FIG. 8 is a schematic diagram of the left channel limiter drive circuitry of such system.

FIG. 8 shows the left limiter drive circuitry portion of left limiter 226, which creates the left limiter control 420. For the primary limiting function, the sensing signal comes from the input to the output amplifier 242. This signal is input to amplifier U10A through series resistors selected under software control by U9 to select the possible limiter signal threshold settings. The signal from U10A goes to level-sensing rectifier stage U11A, Q5A, Q5B and associated components. R102, C67 produce a high frequency roll-off, and C58, R100 produce a low frequency roll-off that together approximate an A-weighting frequency response, making the limiting function sensitive to an approximately A-weighted signal level. From this weighted signal and the rectifier stage, a voltage is induced on C59 that indicates the short-term average signal level. The attack time of this level-sensing is controlled by the size of the signal level increase in combination with the effective resistance of Q5B in series with R109. The resistance of Q5B lowers with increasing current through it, which increases with greater differences between the indicated momentary signal level at the output of U11A and the indicated short-term average level indicated by the voltage on C59. The net effect is an adaptive attack time that is shorter with larger signal increases over the short-term average. U11B and associated components shifts and scales the voltage on C59 to what is appropriate for control of Q1A (FIG. 7). Trimmer R121 provides adjustment to compensate for the tolerances in the control voltage characteristic of matched JFETs Q1A, Q1B.

The secondary limiting function prevents audible clipping at various points in the signal chain. The base-emitter thresholds of Q6A, Q6B, Q7A, Q7B, Q8A, Q8B and their associated circuitry, including Q4A, Q4B, enable this by sensing peak bipolar levels at the limiter amplifier output 254, the output amplifier input 242, and an output amplifier intermediate point 258. When the onset of clipping at any of these points is sensed, current is fed through R119 to rapidly raise the voltage on C59 to reduce the channel gain.

Switch U12, when open, allows the left channel and right channel limiter controls to stay separate and therefore for their associated limiters to operate independently, or, when closed, shorts together the two channel limiter controls to link the left and right limiter actions. In this latter case, the voltage that would be higher between the two channels and thus directing stronger limiting determines the control of both left and right limiters, yielding the same degree of gain reduction in both channels.

Figure 10B:
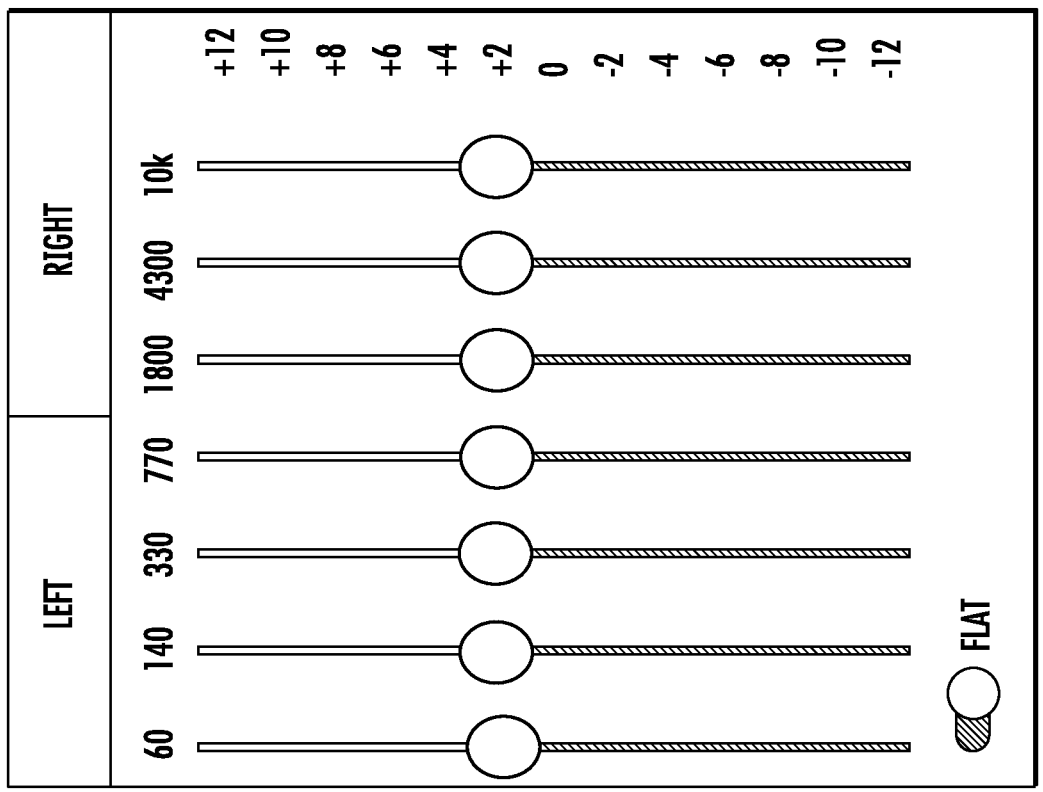
FIGS. 10*a* and 10*b* are examples of smartphone screens for control of frequency equalization.
Figure 10A:
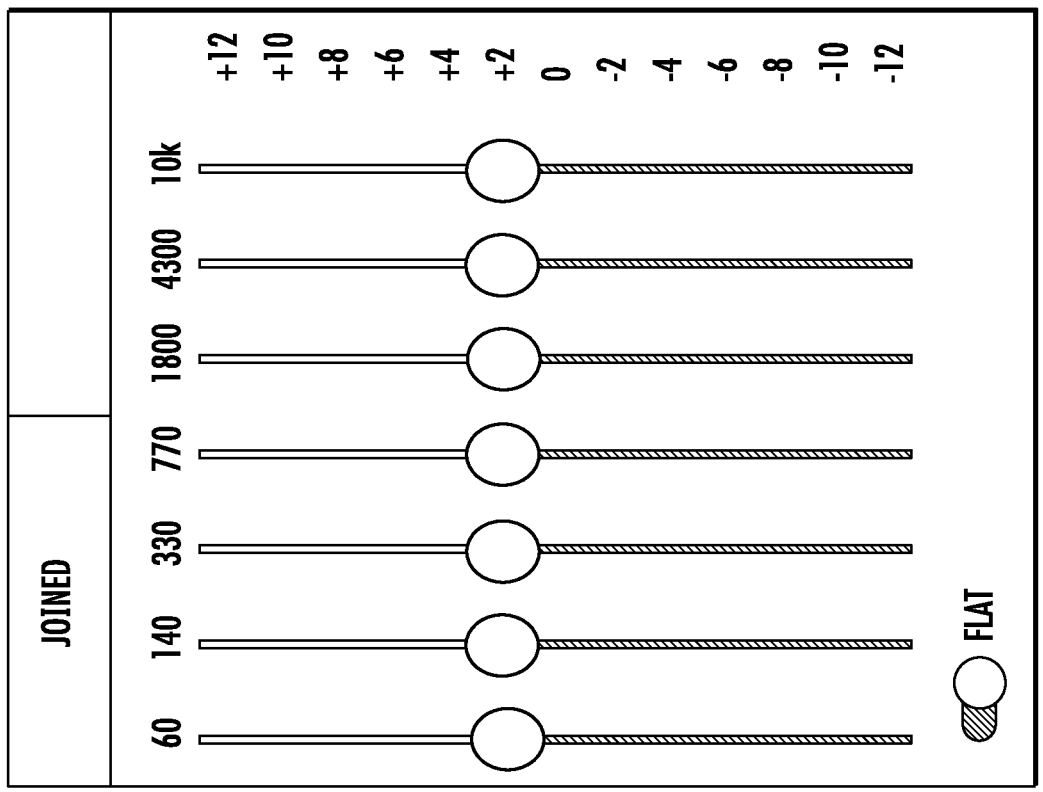
Figure 11:
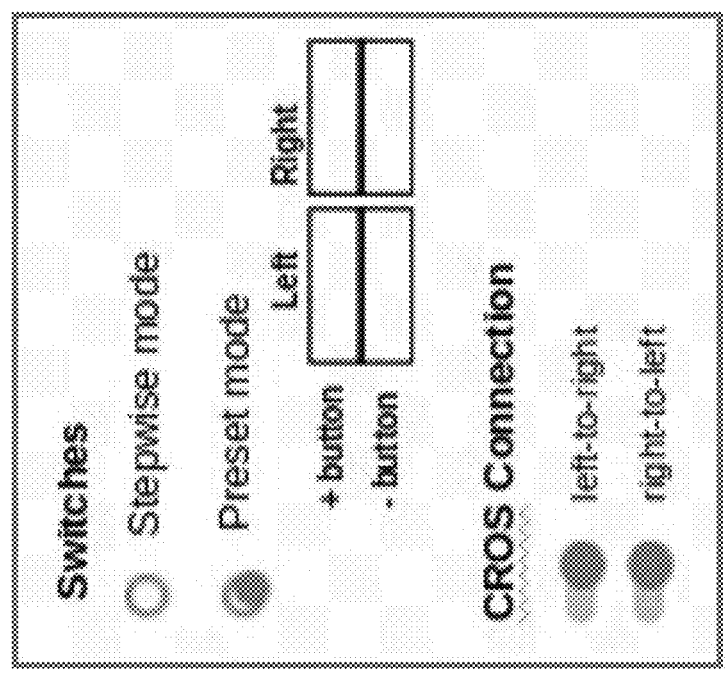
FIG. 11 is an example of a smartphone screen for control of body pack switch functionality and CROS connection.

FIG. 9-11 illustrate possible smartphone touchscreens for user control of system settings. These settings are transferred into the body pack through connection 138 (FIG. 1) and stored there for system operation without the smartphone connected. FIG. 9*a* shows a screen that controls both left and right microphone gains and limiter thresholds together to the same settings. FIG. 9*b* shows the controls for these functions with the channels separated. A separate on-screen button (not shown) allows the user to switch between the joined and separated modes. The limiter action link/unlink UR control is available on both screens and is independent of whether the joined or separated mode is selected.

FIG. 10*a* shows a screen that controls the seven-band frequency equalization with the left and right channels joined for common control. FIG. 10*b* shows a similar screen, but with touch controls to select control of left and right channel equalization independently. A separate control to rapidly return to flat equalization (all bands at 0) engages the hardware switch to bypass the EQ block. The EQ block is also bypassed if all of the bands in both channels are manually set to 0. Both let and right channels always have their EQ blocks engaged or bypassed together, to avoid inserting the small signal latency of the digital signal conversion and processing in one channel only.

FIG. 11 shows a screen that addresses two options. The first option controls whether the body pack up 0.142 and down 0.144 buttons (FIG. 1) move the microphone gain up and down by each step shown in FIG. 9, or toggle between a high and a low level that the user can preset. The second option on the screen allows the user to switch in either the left-to-right or the right-to-left CROS function. The software prevents the user from engaging both at the same time.

The matter set forth in the foregoing description and accompanying drawings is offered by way of illustration only and not as a limitation. While particular embodiments have been shown and described, it will be apparent to those skilled in the art that changes and modifications may be made without departing from the broader aspects of applicants' contribution. The actual scope of the protection sought is intended to be defined in the following claims when viewed in their proper perspective based on the prior art.

What is claimed is:

1. A hearing protection and enhancement system comprising:
   first and second earpieces, each earpiece having an outward-facing microphone for generating a signal representative of sound external to a user and an inward-facing receiver;
   a central signal processing unit coupled to the first and second earpieces for providing electronic control of signal processing parameters of each earpiece signal;
   a portable electronic device connected to the central signal processing unit;
   an amplifier for amplifying the signal from the microphones of each of the first and second earpieces;
   a limiter coupled between the amplifier and an equalizer to reduce the dynamic range of the signal from the microphones of each of the first and second earpieces to remain within the capabilities of the following processing and output circuitry and wherein the limiter in each earpiece rapidly responds to the onset of clipping within the signal chain; and
   an interface allowing communication between the portable electronic device and the central signal processing unit;
   wherein the signal processing parameters for the earpieces can be set by the portable electronic device and stored to the central signal processing unit via the interface to allow the portable electronic device to be disconnected from the central signal processing unit.

2. The hearing protection and enhancement system of claim 1, wherein the portable electronic device is wirelessly connected to the central signal processing unit.

3. The hearing protection and enhancement system of claim 1, wherein the portable electronic device is detachably wired to the central signal processing unit.

4. The hearing protection and enhancement system of claim 1, further comprising an external up switch and an external down switch positioned on the central signal processing unit.

5. The hearing protection and enhancement system of claim 4, wherein the external up and down switches control microphone gain for the first and second earpieces.

6. The hearing protection and enhancement system of claim 4, wherein the external up and down switches toggle between preset microphone gain settings.

7. The hearing protection and enhancement system of claim 1, wherein the signal processing parameters include frequency equalization.

8. The hearing protection and enhancement system of claim 1, wherein the limiter reduces signal levels above a predetermined threshold.

9. The hearing protection and enhancement system of claim 8, wherein the limiter responds to a short-term average signal level appearing at a user's ears.

10. The hearing protection and enhancement system of claim 8, wherein the limiter responds to signal level increases with an adaptive attack time.

11. The hearing protection and enhancement system of claim 8, wherein the limiter responds to an approximately A-weighted signal level.

12. The hearing protection and enhancement system of claim 1, wherein the limiter precedes a frequency equalization block, output amplifiers and earpiece receivers.

13. The hearing protection and enhancement system of claim 12, wherein the limiter limits signals to a level accepted by the frequency equalization block, output amplifiers and earpiece receivers without clipping or overload.

14. The hearing protection and enhancement system of claim 1, wherein the limiter in each earpiece is placed after a mic gain-determining resistor to prevent overload with mic gain increases.

15. The hearing protection and enhancement system of claim 1, further comprising:
    a first switch configured to feed a signal from the microphone of the first earpiece to be combined with a signal from the microphone of the second earpiece when the first switch is activated; and
    a second switch configured to feed the signal from the microphone of the second earpiece to be combined with the signal from the microphone of the first earpiece when the second switch is activated.

16. The hearing protection and enhancement system of claim 1, wherein a microphone gain of the microphone of each the first and second earpieces is controlled by a joined setting.

17. The hearing protection and enhancement system of claim 1, wherein a microphone gain of the microphone of each the first and second earpieces is controlled by separate settings.

18. The hearing protection and enhancement system of claim 8, wherein the predetermined threshold for each of the first and second earpieces is controlled by a joined setting.

19. The hearing protection and enhancement system of claim 8, wherein the predetermined threshold for each of the first and second earpieces is controlled by separate settings.

20. The hearing protection and enhancement system of claim 8, further comprising a limiting action which is linked between the first and second earpieces.

21. The hearing protection and enhancement system of claim 8, further comprising a limiting action which is unlinked between the first and second earpieces.

22. The hearing and enhancement system of claim 7, wherein the frequency equalization of each of the first and second earpieces is controlled by a joined setting.

23. The hearing and enhancement system of claim 7, wherein the frequency equalization of each of the first and second earpieces is controlled by separate settings.

* * * * *